United States Patent
Devin-Baudoin et al.

(10) Patent No.: US 7,510,705 B2
(45) Date of Patent: *Mar. 31, 2009

(54) PROCESS FOR PERMANENTLY RESHAPING THE HAIR USING PARTICULAR AMINOSILICONES

(75) Inventors: Priscille Devin-Baudoin, Vanves (FR); Anne Sabbagh, Rueil Malmaison (FR)

(73) Assignee: L'Oreal, S.A., Paris (FR)

( * ) Notice: Subject to any disclaimer, the term of this patent is extended or adjusted under 35 U.S.C. 154(b) by 22 days.

This patent is subject to a terminal disclaimer.

(21) Appl. No.: 11/524,512

(22) Filed: Sep. 21, 2006

(65) Prior Publication Data

US 2007/0202065 A1    Aug. 30, 2007

Related U.S. Application Data

(63) Continuation of application No. 10/290,189, filed on Nov. 8, 2002, now abandoned.

(30) Foreign Application Priority Data

Nov. 8, 2001    (FR) .................................. 01 14478

(51) Int. Cl.
    *A61Q 5/04*    (2006.01)
(52) U.S. Cl. ................................ 424/70.12; 424/70.2
(58) Field of Classification Search ....................... None
    See application file for complete search history.

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,723,248 A | 11/1955 | Wright |
| 2,781,354 A | 2/1957 | Mannheimer |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,070,533 A | 1/1978 | Papantoniou et al. |
| 4,075,136 A | 2/1978 | Schaper |
| 4,076,912 A | 2/1978 | Papantoniou et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,157,388 A | 6/1979 | Christiansen |
| 4,165,367 A | 8/1979 | Chakrabarti |
| 4,172,887 A | 10/1979 | Vanlerberghe et al. |
| 4,217,914 A | 8/1980 | Jacquet et al. |
| 4,223,009 A | 9/1980 | Chakrabarti |
| 4,237,243 A | 12/1980 | Quack et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |

(Continued)

FOREIGN PATENT DOCUMENTS

| | | |
|---|---|---|
| AU | 200039428 B2 | 2/2001 |
| EP | 0 122 324 | 10/1984 |
| EP | 0 227 994 | 9/1989 |
| EP | 0 342 834 | 11/1989 |
| EP | 0 486 135 | 5/1992 |

(Continued)

OTHER PUBLICATIONS

"Encyclopedia of Chemical Technology", Kirk-Othmer, Third Edition, 1982, vol. 15, pp. 439-458.
"Encyclopedia of Chemical Technology", Kirk-Othmer, Third Edition, 1982, vol. 22, pp. 332-433.
"Encyclopedia of Chemical Technology", Kirk-Othmer, Third Edition, 1982, vol. 3, pp. 896-900.
"Industrial Gums—Polysaccharides and their Derivatives", edited by Roy L. Whistler, Second Edition, Academic Press.
"Polymers in Nature", E.A. MacGregor & C.T. Greenwood, John Wiley & Sons, Chapter 6, pp. 240-328, 1980.

(Continued)

*Primary Examiner*—Jyothsna A Venkat
(74) *Attorney, Agent, or Firm*—Finnegan, Henderson, Farabow, Garrett & Dunner, L.L.P.

(57) ABSTRACT

A process for permanently reshaping keratin fibers, comprising the application to the keratin fibers, before reducing and/or after the fixing, of a pre-treatment and/or post-treatment cosmetic composition comprising, in a cosmetically acceptable medium, at least one aminosilicone, as defined herein, in non-microemulsified form.

39 Claims, No Drawings

U.S. PATENT DOCUMENTS

| | | | |
|---|---|---|---|
| 4,509,949 A | 4/1985 | Huang et al. | |
| 4,591,610 A | 5/1986 | Grollier | |
| 4,608,250 A | 8/1986 | Jacquet et al. | |
| 4,673,568 A | 6/1987 | Grollier et al. | |
| 4,693,935 A | 9/1987 | Mazurek | |
| 4,702,906 A | 10/1987 | Jacquet et al. | |
| 4,710,314 A | 12/1987 | Madrange et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,770,873 A | 9/1988 | Wolfram et al. | |
| 4,839,166 A | 6/1989 | Grollier et al. | |
| 4,957,732 A | 9/1990 | Grollier et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,057,311 A | 10/1991 | Kamegai et al. | |
| 5,061,289 A | 10/1991 | Clausen et al. | |
| 5,077,040 A | 12/1991 | Bergmann et al. | |
| 5,085,860 A | 2/1992 | Junino et al. | |
| 5,089,252 A | 2/1992 | Grollier et al. | |
| 5,106,612 A | 4/1992 | Maignan et al. | |
| 5,139,037 A | 8/1992 | Grollier et al. | |
| 5,154,918 A | 10/1992 | Maignan et al. | |
| 5,196,189 A | 3/1993 | Jacquet et al. | |
| 5,210,324 A | 5/1993 | Farrar et al. | |
| 5,340,367 A | 8/1994 | Schultz et al. | |
| 5,344,464 A | 9/1994 | Madrange et al. | |
| 5,380,340 A | 1/1995 | Neunhoeffer et al. | |
| 5,466,878 A | 11/1995 | Junino et al. | |
| 5,534,267 A | 7/1996 | Neunhoeffer et al. | |
| 5,538,717 A | 7/1996 | De La Poterie | |
| 5,583,257 A | 12/1996 | Junino et al. | |
| 5,626,840 A | 5/1997 | Thomaides et al. | |
| 5,663,366 A | 9/1997 | Neunhoeffer et al. | |
| 5,708,151 A | 1/1998 | Mockli | |
| 5,741,337 A | 4/1998 | Bone et al. | |
| 5,756,076 A | 5/1998 | Cervantes et al. | |
| 5,766,576 A | 6/1998 | Lowe et al. | |
| 5,773,611 A | 6/1998 | Zysman et al. | |
| 5,833,997 A | 11/1998 | Mahieu et al. | |
| 5,925,341 A | 7/1999 | Cervantes et al. | |
| 5,958,392 A | 9/1999 | Grollier et al. | |
| 5,976,195 A | 11/1999 | De La Mettrie et al. | |
| 6,010,541 A | 1/2000 | De La Mettrie | |
| 6,071,504 A | 6/2000 | Kawai et al. | |
| 6,099,592 A | 8/2000 | Vidal et al. | |
| 6,099,593 A | 8/2000 | Terranova et al. | |
| 6,143,286 A | 11/2000 | Bhambhani et al. | |
| 6,177,090 B1 | 1/2001 | Dubief et al. | |
| 6,179,881 B1 | 1/2001 | Henrion et al. | |
| 6,214,326 B1 | 4/2001 | Dupuis | |
| 6,241,784 B1 * | 6/2001 | De La Mettrie et al. | 8/406 |
| 6,254,646 B1 | 7/2001 | De La Mettrie et al. | |
| 6,260,556 B1 | 7/2001 | Legrand et al. | |
| 6,284,003 B1 | 9/2001 | Rose et al. | |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 6,471,953 B1 | 10/2002 | N'Guyen et al. | |
| 6,479,042 B1 | 11/2002 | Nguyen et al. | |
| 6,506,373 B1 * | 1/2003 | Dannecker et al. | 424/70.2 |
| 6,511,669 B1 | 1/2003 | Garnier et al. | |
| 6,582,477 B1 | 6/2003 | Plos | |
| 6,613,313 B2 | 9/2003 | Kimura | |
| 6,770,271 B2 | 8/2004 | Mondet et al. | |
| 6,824,764 B2 * | 11/2004 | Devin-Baudoin et al. | 424/70.1 |
| 6,824,765 B2 * | 11/2004 | Gawtrey et al. | 424/70.1 |
| 6,846,333 B2 * | 1/2005 | Legrand et al. | 8/405 |
| 6,916,467 B2 | 7/2005 | Devin-Baudoin et al. | |
| 7,128,902 B2 * | 10/2006 | Legrand et al. | 424/70.122 |
| 7,135,167 B2 * | 11/2006 | Legrand et al. | 424/70.122 |
| 7,138,109 B2 | 11/2006 | Devin-Baudoin et al. | |
| 7,220,408 B2 * | 5/2007 | Decoster et al. | 424/70.12 |
| 7,223,385 B2 | 5/2007 | Gawtrey et al. | |
| 2002/0006389 A1 | 1/2002 | Restle et al. | |
| 2002/0187117 A1 | 12/2002 | Devin-Baudoin et al. | |

FOREIGN PATENT DOCUMENTS

| | | |
|---|---|---|
| EP | 0 412 707 | 2/1994 |
| EP | 0 582 152 | 2/1994 |
| EP | 0 646 572 | 4/1995 |
| EP | 0 412 704 | 4/1999 |
| GB | 0 839 805 | 6/1960 |
| GB | 0 922 457 | 4/1963 |
| GB | 1 021 400 | 3/1966 |
| GB | 1 026 978 | 4/1966 |
| GB | 1 153 196 | 5/1969 |
| GB | 1 486 576 | 9/1977 |
| GB | 1 546 809 | 5/1979 |
| GB | 2 141 454 | 12/1984 |
| GB | 2 165 550 | 4/1986 |
| GB | 2 058 103 | 4/1991 |
| WO | WO 93/23446 | 11/1993 |
| WO | WO 94/07844 | 4/1994 |
| WO | WO 94/10131 | 5/1994 |
| WO | WO 94/24097 | 10/1994 |
| WO | WO 95/00578 | 1/1995 |
| WO | WO 95/01772 | 1/1995 |
| WO | WO 95/15144 | 6/1995 |
| WO | WO 95/16665 | 6/1995 |

OTHER PUBLICATIONS

"Volatile Silicone Fluids for Cosmetic Formulations", Cosmetics and Toiletries, vol. 91, Jan. 1976, pp. 27-32.
Dorgan, "Waxes in Cosmetics", Drug and Cosmetic Industry, Dec. 1983, pp. 30-33.
Porter, Handbook of Surfactants 116-178 (Blackie & Son 1991).
U.S. Appl. No. 10/290,149, filed Nov. 8, 2002, now abandoned.
U.S. Appl. No. 10/290,159, filed Nov. 8, 2002, now abandoned.
U.S. Appl. No. 10/290,192, filed Nov. 8, 2002, now abandoned.
U.S. Appl. No. 10/290,226, filed Nov. 8, 2002, now abandoned.
U.S. Appl. No. 10/290,342, filed Nov. 8, 2002, now abandoned.
U.S. Appl. No. 10/290,343, filed Nov. 8, 2002, now abandoned.
U.S. Appl. No. 10/290,345, filed Nov. 8, 2002, now abandoned.
U.S. Appl. No. 11/158,014, filed Jun. 22, 2005, now abandoned.
Copending U.S. Appl. No. 11/706,261, filed Feb. 15, 2007.
Copending U.S. Appl. No. 11/706,399, filed Feb. 15, 2007.
English language Derwent Abstract of DE 197 54 053, Jun. 10, 1999.
English language Derwent Abstract of DE 42 29 922, Mar. 10, 1994.
English language Derwent Abstract of 44 02 929, Jun. 22, 1995.
English language Derwent Abstract of DE 44 20 736, Aug. 10, 1995.
English language Derwent Abstract of DE 44 24 530, Jan. 18, 1996.
English language Derwent Abstract of DE 44 24 533, Jan. 18, 1996.
English language Derwent Abstract of EP 0 080 976, Jun. 8, 1983.
English language Derwent Abstract of EP 0 225 261, Jun. 10, 1987.
English language Derwent Abstract of EP 0 368 763, May 16, 1990.
English language Derwent Abstract of EP 0 765 655, Apr. 2, 1987.
English language Derwent Abstract of FR 2 679 448, Jan. 29, 1993.
English language Derwent Abstract of FR 2 679 558, Jan. 29, 1993.
English language Derwent Abstract of JP 2001-10936 A, Jan. 16, 2001.
English language Derwent Abstract of JP 2-250814, Oct. 8, 1990.
English language Derwent Abstract of JP 4-154713 A, May 27, 1992.
English language Derwent Abstract of JP 8-157340 A, Jun. 18, 1996.
English language Derwent Abstract of JP 9-151120, Jun. 10, 1997.
English language JAPIO Abstract of JP 2-019576, Jan. 23, 1990.
English language JAPIO Abstract of JP 9-110659, Apr. 28, 1997.
English language Patent Abstract of Japan of JP 2001-10935, Jan. 16, 2001.
French Search Report for FR 0 114 468, dated Aug. 8, 2002.
French Search Report for FR 0 114 469, dated Aug. 22, 2002.

French Search Report for FR 0 114 470, dated Sep. 18, 2002.
French Search Report for FR 0 114 472, dated Aug. 30, 2002.
French Search Report for FR 0 114 473, dated Sep. 16, 2002.
French Search Report for FR 0 114 474, dated Aug. 8, 2002.
French Search Report for FR 0 114 476, dated Sep. 20, 2002.
French Search Report for FR 0 114 477, dated Sep. 20, 2002.
French Search Report for FR 0 114 478, dated Sep. 18, 2002.
French Search Report for FR 0 114 479, dated Sep. 16, 2002.
French Search Report for FR 0 114 480, dated Aug. 9, 2002.
French Search Report for FR 0 114 481, dated Sep. 4, 2002.
French Search Report for FR 0 114 482, dated Aug. 28, 2002.
French Search Report for FR 0 114 484, dated Sep. 4, 2002.
French Search Report for FR 0 114 485, dated Aug. 29, 2002.
French Search Report for FR 0 114 486, dated Sep. 23, 2002.
Office Action in U.S. Appl. No. 10/290,149, dated Apr. 30, 2004, now abandoned.
Office Action in U.S. Appl. No. 10/290,149, dated Nov. 4, 2004, now abandoned.
Office Action in U.S. Appl. No. 10/290,159, dated Dec. 27, 2004, now abandoned.
Office Action in U.S. Appl. No. 10/290,159, dated May 3, 2004, now abandoned.
Office Action in U.S. Appl. No. 10/290,192, dated Jan. 11, 2006, now abandoned.
Office Action in U.S. Patent No. 7,128,902, dated Jan. 11, 2006.
Office Action in U.S. Appl. No. 10/290,226, dated Apr. 19, 2006, now abandoned.
Office Action in U.S. Patent No. 7,138,109, dated Jan. 11, 2006.
Office Action in U.S. Appl. No. 10/290,342, dated Jan. 25, 2006, now abandoned.
Office Action in U.S. Appl. No. 10/290,343, dated Jan. 25, 2006, now abandoned.
Office Action in U.S. Appl. No. 10/290,345, dated Feb. 9, 2006, now abandoned.
Office Action in U.S. Patent No. 7,220,408, dated Apr. 19, 2006.
Office Action in U.S. Patent No. 7,135,167, dated Jan. 10, 2006.
Office Action in U.S. Patent No. 7,223,385, dated Apr. 19, 2006.
Office Action in co-pending U.S. Appl. No. 11/706,261, dated Jul. 10, 2008.
Office Action in co-pending U.S. Appl. No. 11/706,399, dated Jul. 9, 2008.

* cited by examiner

PROCESS FOR PERMANENTLY RESHAPING THE HAIR USING PARTICULAR AMINOSILICONES

This is a continuation of application Ser. No. 10/290,189, filed Nov. 8, 2002, now abandoned which claims the benefit of priority of French Patent Application No. 01 14478, filed Nov. 8, 2001, both of which are incorporated herein by reference.

The present disclosure relates to a process for permanently reshaping keratin fibres, for example, hair. This process may be used, for example, in professional hairstyling salons, or privately via the marketing of kits.

The expression "permanent reshaping process" means any long-lasting process for shaping, curling, straightening or relaxing the hair.

The expression "keratin fibres" means, for example, hair, eyelashes and eyebrows.

One technique for obtaining a permanent reshaping of the hair comprises, in a first stage, opening the keratin —S—S— disulphide (cystine) bonds using a reducing composition comprising a reducing agent (reduction), followed, for example, after having rinsed the hair thus treated, by reconstituting, in a second stage, the disulphide bonds by applying to the hair, which has been placed under tension beforehand (for example, with curlers and the like), an oxidizing composition (oxidizing, also known as fixing) so as to finally give the hair the desired shape. This technique thus can make it equally possible either to make the hair wavy or to straighten or relax it. The new shape given to the hair by a chemical treatment such as above can be long-lasting and may, for example, withstand the action of washing with water and/or shampoos, as opposed to other techniques for temporary reshaping, such as hairsetting.

The reducing composition that may be used to carry out the reduction of a permanent-waving process may comprise, as reducing agents, sulphites, bisulphites or thiols. Among the thiols that may be mentioned are cysteine and its various derivatives, cysteamine and its derivatives, thiolactic acid, thioglycolic acid and its esters, such as glyceryl monothioglycolate, and thioglycerol.

As to the oxidizing composition used to carry out the fixing, compositions based on aqueous hydrogen peroxide solution or alkali metal bromates may be used.

One disadvantage of the permanent-waving techniques known to date is that applying them repeatedly to the hair may induce in the long term a gradual deterioration in the quality of the hair, for example, a gradual and pronounced deterioration in the sheen and the cosmetic properties of the hair, such as the softness of the fibres, which may have a tendency to become more and more coarse, and also as regards their disentangling, the hair may become more and more difficult to disentangle. This deterioration may be pronounced when the fixing of the permanent-waving process is carried out using a bromate.

To limit this deterioration of the hair, it has already been proposed to introduce conditioners directly into the reducing composition. For example, Japanese patent applications H2-250814 and H9-151120 describe reducing compositions containing aminosilicones, which may optionally be in the form of a microemulsion.

However, processes for permanently reshaping the hair using such compositions are not always entirely satisfactory, since the degree, the quality and liveliness of the curls may be insufficient and short-lived, for example, if the conditioner, such as aminosilicones, directly combined with the reducing agent to block the activity of the reducing agent.

The present disclosure addresses at least one of these disadvantages by providing a process for permanently reshaping keratin fibres, such as hair, which can reduce the degree of mechanical and/or cosmetic degradation of the hair, while at the same time providing a satisfactory degree, quality and liveliness of curls.

The inventors have discovered, surprisingly and unexpectedly, that by applying to the hair, before applying the reducing composition and/or after having applied the oxidizing composition, at least one pre-treatment and/or post-treatment cosmetic composition comprising at least one aminosilicone as defined below, it is possible to solve at least one of the problems.

One new embodiment is a process for permanently reshaping keratin fibres, such as hair, comprising the following:

(i) applying a reducing composition to the keratin fibres; and (ii) oxidizing the keratin fibres;

wherein the process also comprises applying to the keratin fibres, before (i) and/or after (ii), a pre-treatment and/or post-treatment cosmetic composition comprising, in a cosmetically acceptable medium, at least one aminosilicone in non-microemulsified form chosen from the following aminosilicones of formulae (I) and (II):

Aminosilicones of Formula (I)

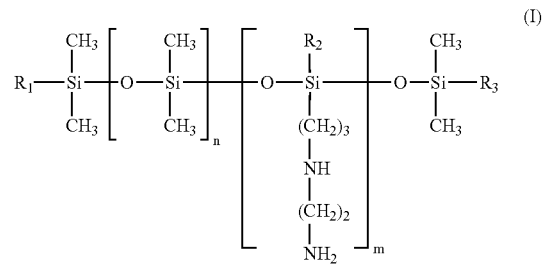

in which:

m and n are numbers such that the sum (n+m) range, from 1 to 1 000, such as from 50 to 250 and further such as from 100 to 200;

n is a number ranging from 0 to 999, and further, for example, from 49 to 249 and even further, for example, from 125 to 175; m is number ranging from 1 to 1 000, and further, for example, from 1 to 10, and even further, for example, from 1 to 5;

$R_1$, $R_2$, $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals.

In one embodiment, the alkoxy radical is a methoxy radical.

The hydroxyl/alkoxy molar ratio may range, for example, from 0.2:1 to 0.4:1 and further, for example, from 0.25:1 to 0.35:1, and even further, for example, is equal to 0.3:1.

The aminosilicone of formula (I) can have a weight-average molecular mass ranging, for example, from 2 000 to 1 000 000, and further, for example, from 3 500 to 200 000.

Aminosilicones of Formula (II)

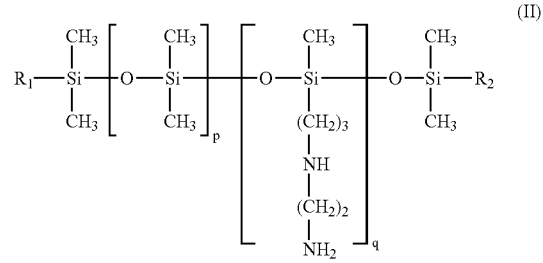

in which:

p and q are numbers such that the sum (p+q) ranges, for example, from 1 to 1 000, such as from 50 to 350 and further such as from 150 to 250;

p is a number ranging from 0 to 999, and further, for example, from 49 to 349, and even further, for example, from 159 to 239; and q is a number ranging from 1 to 1 000, and further, for example, from 1 to 10 and even further, for example, from 1 to 5;

$R_1$, $R_2$, which may be identical or different, are chosen from hydroxyl and $C_1$-$C_4$ alkoxy radicals, wherein at least one of the radicals $R_1$ and $R_2$ is chosen from $C_1$-$C_4$ alkoxy radicals.

In one embodiment, the alkoxy radical is a methoxy radical.

The hydroxyl/alkoxy molar ratio may range, for example, from 1:0.8 to 1:1.1 and further, for example, from 1:0.9 to 1:1, and even further, for example, is equal to 1:0.95.

The aminosilicone of formula (II) may have a weight-average molecular mass ranging, for example, from 2 000 to 200 000, and further, for example, from 5 000 to 100 000, and even further, for example, from 10 000 to 50 000.

The weight-average molecular masses of these aminosilicones are measured by Gel Permeation Chromatography (GPC) at room temperature as polystyrene equivalent. The columns used are μ styragel columns. The eluent is THF, the flow rate is 1 ml/min. 200 μl of a solution containing 0.5% by weight of silicone in THF are injected. The detection is made by refractometry and UVmetry.

The expression "non-microemulsified" means a silicone used as it is or in the form of an emulsion in the presence of at least one surfactant, the number-average size of the silicone particles in the emulsion being greater than 70 nm, ranging, for example, from 70 to 500 nm. One of ordinary skill in the art can measure such particle sizes by known methods. Such particle sizes are measured with a laser granulometer.

The surfactant may be of any type, such as cationic and/or nonionic.

Another new embodiment relates to a kit for permanently reshaping keratin fibres, comprising at least one compartment comprising a pre-treatment and/or post-treatment cosmetic composition comprising at least one aminosilicone as defined above.

The commercial products corresponding to these aminosilicones of formula (I) or (II) may include in their composition at least one other aminosilicone whose structure is different from the formulae (I) and (II).

A product containing aminosilicones of formula (I) is proposed by the company Wacker under the name Belsil ADM 652®.

Products containing aminosilicones of formula (II) are proposed by the company Wacker under the names Fluid WR 1300® and Finish WR 1300.

In one embodiment, the at least one aminosilicone chosen from formulae (I) and (II) is chosen such that the contact angle with water of hair treated with a composition comprising 2% AM (active materials) of the aminosilicone ranges, for example, from 90 to 180°, and such as from 90 to 130°. As used herein, a range "from x to y" includes within the range the endpoints x and y.

In another embodiment, the composition comprising at least one aminosilicone chosen from aminosilicones of formulae (I) and (II) is chosen such that the contact angle of hair treated with the composition ranges, for example, from 90 to 180° such as from 90 to 130°.

The measurement of the contact angle is based on the immersion of hair in distilled water. The measurement includes evaluating the force exerted by the water on the hair during its immersion in distilled water and during its removal. The forces thus measured are directly linked to the contact angle θ between the water and the surface of the hair. The hair is said to be hydrophilic when the angle θ ranges from 0 to less than 90°, and hydrophobic when this angle ranges from 90° to 180°.

The test is carried out with locks of natural hair which have been bleached under the same conditions and then washed.

Each mesh of 1 g is placed in a crystallizing dish 75 mm in diameter and then homogeneously coated with 5 ml of the formula to be tested. The lock is thus left for 15 minutes at room temperature and then rinsed for 30 seconds. The drained lock is left in the open air until it is completely dry.

For each evaluation, 10 hair strands which have undergone the same treatment are analysed. Each sample, attached to a precision microbalance, is immersed by the tip in a container filled with distilled water. This DCA balance (Dynamic Contact Angle Analyser), from the company Cahn Instruments, makes it possible to measure the force (F) exerted by the water on the hair.

In parallel, the perimeter of the hair (P) is measured via a microscopy observation.

The mean wettability force on 10 hair strands and the section of hair analysed make it possible to obtain the contact angle of the hair on the water, according to the formula:

$$F = P * \Gamma lv * \cos \theta$$

where F is the wettability force expressed in Newtons, P the perimeter of the hair in metres, $\Gamma lv$ the liquid/steam interfacial tension of the water in $J/m^2$ and θ the contact angle. The product SLM 28020® from Wacker at 12% in water (that is 2% as active materials) gives a contact angle of 93° according to the test indicated above.

In one embodiment, the concentration of the at least one aminosilicone in the pre-treatment and/or post-treatment composition ranges, for example, from 0.05 to 10% by weight relative to the total weight of the composition, such as from 0.1 to 7% by weight relative to the total weight of the composition.

The pre-treatment and/or post-treatment composition comprising at least one aminosilicone may further comprise at least one active agent chosen from water-soluble and liposoluble active agents, having cosmetic and/or dermopharmaceutical activity. Non-limiting examples of those active agents include vitamins and derivatives thereof such as vitamin E, vitamin E acetate, vitamin C and its esters, the B vitamins, vitamin A alcohol and retinol, vitamin A acid and retinoic acid and its derivatives, provitamins such as panthenol, vitamin A palmitate, niacinamide, ergocalciferol, antioxidants, essential oils, wetting agents, silicone and non-silicone sunscreens, preserving agents, sequestering agents, pearlescent agents, pigments, moisturizers, anti-dandruff agents, anti-seborrhoeic agents, plasticizers, hydroxy acids, electrolytes, solvents and fragrances.

The composition may also comprise at least one solvent, such as C1-C8 lower alcohols such as ethanol.

The pH of the pretreatment and/or post-treatment composition comprising at least one aminosilicone ranges, for example, from 2 to 10, such as from 3 to 9.

In one embodiment, the pre-treatment composition comprising at least one aminosilicone as defined above is applied to the hair to be treated, which will optionally have been moistened beforehand. This application may be performed after the usual procedure of placing the hair under tension in a shape corresponding to the desired final shape for the hair (for example curls), This procedure itself can possibly be carried out by any means, such as a mechanical means, that is suitable and known per se for maintaining hair under tension, such as rollers, curlers and the like.

In another embodiment, the pre-treatment and/or post-treatment composition comprising at least one aminosilicone is left to act on the hair, at room temperature or under heat, for a period of time ranging from, for example, 1 to 60 minutes, such as from 3 to 30 minutes.

According to an option in the process, the hair impregnated with the pre-treatment composition comprising at least one aminosilicone can be rinsed, wherein the rinsing can be carried out using water.

In the process, a reducing composition is applied to the hair, wherein the reducing composition may comprise at least one thiol.

The thiol in the reducing composition may be chosen from thiols known as reducing agents such as thioglycolic acid, glyceryl and glycol monothioglycolate, cysteamine and its $C_1$-$C_4$ acyl derivatives such as N-acetylcysteamine or N-propionyl-cysteamine, cysteine, N-acetylcysteine, sugar N-mercaptoalkylamides such as N-(2-mercaptoethyl)gluconamide, 3-mercaptopropionic acid and its derivatives, thiolactic acid and its esters such as glyceryl monothiolactate, thiomalic acid, pantethine, thioglycerol, alkali metal and alkaline-earth metal sulphites and bisulphites, the N-(mercaptoalkyl)-ω-hydroxyalkylamides described in patent application EP-A-354 835 and the N-mono- or N,N-dialkylmercapto-4-butyramides described in patent application EP-A-368 763, the aminomercaptoalkylamides described in patent application EP-A-432 000, the N-(mercaptoalkyl)succinamic acid and N-(mercaptoalkyl)succinimide derivatives described in patent application EP-A-465 342, the alkylaminomercaptoalkylamides described in patent application EP-A-514 282, and the mixture of 2-hydroxypropyl thioglycolate and of 2-hydroxy-1-methylethyl thioglycolate described in patent application FR-A-2 679 448.

In one embodiment, thioglycolic acid, thiolactic acid and 3-mercaptopropionic acid are chosen for use.

The reducing agent may be present in a concentration that may range, for example, from 1% to 20% by weight relative to the total weight of the reducing composition.

The pH of the reducing composition may range, for example, from 6 to 10, and further, for example, from 7 to 9.

The pH values of the reducing compositions may be conventionally adjusted by adding at least one basifying agent. Non-limiting examples of such basifying agents include aqueous ammonia, monoethanolamine, diethanolamine, triethanolamine, iso-propanolamine, 1,3-propanediamine, ammonium and alkali metal carbonates and bicarbonates, primary, secondary and tertiary amine carbonates and bicarbonates and organic carbonates such as guanidine carbonate.

The reducing composition may be in the form of a thickened or unthickened lotion, a cream, a gel, or any other suitable form, and may comprise additives known for their use in reducing compositions for permanently reshaping the hair.

The reducing composition may also be of the exothermic type, i.e., the type causing a certain level of heating during application to the hair, affording a pleasant sensation to the person on whom the permanent-waving or straightening process is being performed.

The reducing composition may also comprise a solvent such as ethanol, propanol, isopropanol and glycerol, in a maximum concentration of 20% by weight relative to the total weight of the composition.

When the compositions are intended for a hair straightening or relaxing process, the reducing composition may be, for example, in the form of a thickened cream so as to keep the hair as straight as possible. These creams are prepared in the form of "heavy" emulsions, for example, based on glyceryl stearate, glycol stearate, self-emulsifiable waxes, fatty alcohols, etc.

It is also possible to use liquids or gels containing thickeners such as carboxyvinyl polymers or copolymers which can "stick" the hairs together and keep them in the smooth position during the exposure time.

The compositions may also be in a "self-neutralizing" or "self-regulated" form and, in this case, the reducing agents used may be combined with at least one disulphide known for its use in a reducing composition for self-neutralizing permanent waving.

In one non-limiting example, the hair onto which the reducing composition has been applied is left to rest for a few minutes, such as ranging from 2 to 40 minutes and further such as ranging from 5 to 30 minutes, so as to allow the reducing agent sufficient time to act correctly on the hair. This waiting stage may be carried out by leaving the treated hair to rest in the open air (at room temperature or with heating). During this waiting stage, care may be taken to ensure that the hair does not dry out completely but instead remains humid.

The hair impregnated with the reducing composition may then be carefully rinsed, such as with water. Optionally, after rinsing, a stage of heating at high temperature for a few seconds may be carried out.

An oxidizing composition can then be applied to the hair thus rinsed, with the aim of fixing the new shape given to the hair. It may also be envisaged to leave the hair to be oxidized by the air.

The oxidizing composition comprises an oxidizing agent that may be chosen from aqueous hydrogen peroxide solution, alkali metal bromates, persalts and polythionates. As mentioned previously, one of the advantages of an embodiment of the process disclosed is that it can be entirely suitable in the case of bromate-based oxidizing compositions. The bromate concentration in the oxidizing composition ranges, for example, from 0.1 to 2 M.

The pH of the oxidizing composition may range, for example, from 2 to 10.

As in the case of the application of the reducing composition, the hair onto which the oxidizing composition has been applied is then, left for a standing or waiting stage that may last a few minutes, for example, ranging from 3 to 30 minutes and further, for example, ranging from 5 to 15 minutes.

The post-treatment composition comprising at least one aminosilicone as defined above is, for example, applied, after rinsing out the oxidizing composition, to wet or dry hair. The hair that has undergone the post-treatment may optionally be dried and/or heated and/or rinsed, before being styled. Where appropriate, the composition may be applied while the hair is maintained by a mechanical device, for example, hairsetting rollers or curlers.

Usually, the hair impregnated with the oxidizing composition is rinsed carefully, such as with water. Before or after rinsing, the keratin fibres may be separated from the implement used for placing the keratin fibres under tension.

The hair finally obtained can have good cosmetic properties: the hair can be shinier, softer and easier to disentangle or to style.

In one embodiment, the pre-treatment and/or post-treatment composition comprising at least one aminosilicone as defined above is applied according to at least one of the following variants:
  to clean, wet hair, before using the implement for placing the hair under tension, without rinsing the hair before applying the reducing agent; and
  to wet hair after rinsing out the fixing agent, the hair being subsequently either rinsed and/or dried.

When the process for permanently reshaping the hair is a straightening process, it is possible, in a manner that is known per se, to use a straightening agent, such as a thiol agent or an alkaline agent.

In the case of a thiol straightening agent, the process may be carried out, for example, by applying the pre-treatment and/or post-treatment composition comprising at least one aminosilicone as defined above according to at least one of the following variants:

to clean, wet hair, without rinsing before applying the reducing agent; and to clean, wet hair, after rinsing out the fixing agent, by rinsing before drying the hair.

In the case of an alkaline straightening agent, the process may be carried out, for example, by applying the pre-treatment and/or post-treatment composition comprising at least one aminosilicone as defined above to wet hair, after rinsing out neutralizing shampoo, by rinsing before drying the hair.

In the case of a hair curling process, the process can give lively curls, and the hair may be at least one of supple, light, silky and well separated.

In the case of a hair straightening process, the process, for example, may afford control of the body of the hair, may make the hair smooth from the root to the tip and may give a more natural feel.

The present disclosure may be understood more clearly with the aid of the non-limiting examples which follow, which constitute various embodiments of the process.

In the examples, a.m. means active material.

EXAMPLES

1) Care Composition for Straightened Hair

| Ingredients | % a.m. |
| --- | --- |
| cetylstearyl alcohol/sodium lauryl sulphate/cetyl myristate/myristyl alcohol (62/20/8/10) | 12 |
| oxyethylenated oleyl alcohol (20 EO) | 0.1 |
| glycerine | 0.5 |
| polydimethylsiloxane of formula (II) proposed by Wacker under the name Finish WR 1300 | 2 |
| demineralized water | qs 100 g |

This composition was applied to hair straightened with an alkaline straightening agent, after rinsing out the cleansing shampoo. The composition was left for 1 to 10 minutes on the hair before being rinsed out.

2) Protective Care Composition Before Permanent Waving

The composition described in 1) may be used as a pre-permanent-waving treatment. This composition was applied to wet hair before fitting curlers, and was not rinsed out before the application of the permanent-waving reducing agent. This composition could make it possible to limit the degradation of the hair due to permanent waving, while making it possible to obtain tonic curls.

Similar results were obtained by replacing the poly-dimethylsiloxane of formula (II) with an equivalent quantity of polydimethylsiloxane of formula (I) proposed by Wacker under the name Belsil ADM 652.

What is claimed is:

1. A process for permanently reshaping keratin fibers, comprising:
   (i) applying a reducing composition to the keratin fibers; and
   (ii) oxidizing the keratin fibers;
wherein the process further comprises applying to the keratin fibers, before (i) and/or after (ii), a pre-treatment and/or post-treatment cosmetic composition comprising, in a cosmetically acceptable medium, at least one aminosilicone in non-microemulsified form chosen from aminosilicones of formulae (I) and (II) below:

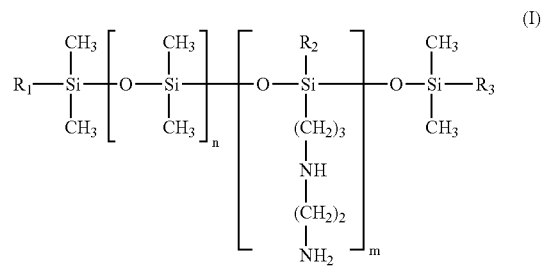

wherein in formula (I):
m and n are numbers such that the sum (n+m) ranges from 1 to 1 000, n is a number ranging from 0 to 999 and m is a number ranging from 1 to 1 000; $R_1$, $R_2$, $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

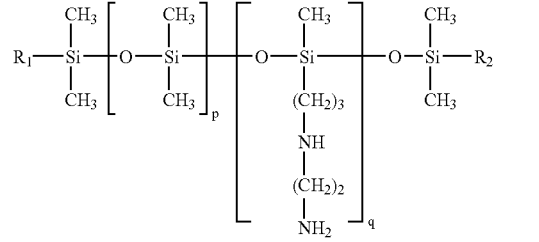

wherein in formula (II):
p and q are numbers such that the sum (p+q) ranges from 1 to 1 000,
p is a number ranging from 0 to 999 and q is a number ranging from 1 to 1 000;
$R_1$, $R_2$, which may be identical or different, are chosen from hydroxyl and $C_1$-$C_4$ alkoxy radicals, wherein at least one of the radicals $R_1$ and $R_2$ is chosen from $C_1$-$C_4$ alkoxy radicals.

2. The process according to claim 1, wherein in formula (I) the sum (n+m) ranges from 50 to 250.

3. The process according to claim 1, wherein in formula (I) the sum (n+m) ranges from 100 to 200.

4. The process according to claim 1, wherein in formula (I) the n is a number ranging from 49 to 249.

5. The process according to claim 1, wherein in formula (I) the n is a number ranging from 125 to 175.

6. The process according to claim 1, wherein in formula (I) the m is a number ranging from 1 to 10.

7. The process according to claim 1, wherein in formula (I) the m is a number ranging from 1 to 5.

8. The process according to claim 1, wherein in formula (II) the sum (p+q) ranges from 50 to 350.

9. The process according to claim 1, wherein in formula (II) the sum (p+q) ranges from 150 to 250.

10. The process according to claim 1, wherein in formula (II) the p is a number ranging from 49 to 349.

11. The process according to claim 1, wherein in formula (II) the p is a number ranging from 159 to 239.

12. The process according to claim 1, wherein in formula (II) the q is a number ranging from 1 to 10.

13. The process according to claim 1, wherein in formula (II) the q is a number ranging from 1 to 5.

14. The process according to claim 1, wherein the $C_1$-$C_4$ alkoxy radical is a methoxy radical.

15. The process according to claim 1, wherein, for the at least one aminosilicone of formula (I), the hydroxyl/alkoxy molar ratio ranges from 0.2:1 to 0.4:1.

16. The process according to claim 15, wherein the hydroxyl/alkoxy molar ratio ranges from 0.25:1 to 0.35:1.

17. The process according to claim 16, wherein the hydroxyl/alkoxy molar ratio is equal to 0.3:1.

18. The process according to claim 1, wherein, for the at least one aminosilicone of formula (II), the hydroxyl/alkoxy molar ratio ranges from 1:0.8 to 1:1.1.

19. The process according to claim 18, wherein the hydroxyl/alkoxy molar ratio ranges from 1:0.9 to 1:1.

20. The process according to claim 19, wherein the hydroxyl/alkoxy molar ratio is equal to 1:0.95.

21. The process according to claim 1, wherein the at least one aminosilicone of formula (I) has a weight-average molecular mass ranging from 2 000 to 1 000 000.

22. The process according to claim 21, wherein the at least one aminosilicone of formula (I) has a weight-average molecular mass ranging from 3 500 to 200 000.

23. The process according to claim 1, wherein the at least one aminosilicone of formula (II) has a weight-average molecular mass ranging from 2 000 to 200 000.

24. The process according to claim 23, wherein the at least one aminosilicone of formula (II) has a weight-average molecular mass ranging from 5 000 to 100 000.

25. The process according to claim 24, wherein the at least one aminosilicone of formula (II) has a weight-average molecular mass ranging from 10 000 to 50 000.

26. The process according to claim 1, wherein the at least one aminosilicone is chosen such that the contact angle with water of keratin fibers treated with a composition comprising 2% AM (active materials) of the at least one aminosilicone ranges from 90 to 180°.

27. The process according to claim 26, wherein the at least one aminosilicone is chosen such that the contact angle with water of keratin fibers treated with a composition comprising 2% AM (active materials) of the at least one aminosilicone ranges from 90 to 130°.

28. The process according claim 1, wherein the composition comprising at least one aminosilicone is chosen such that the contact angle with water of keratin fibers treated with the composition ranges from 90 to 180°.

29. The process according to claim 1, wherein the pH of the pre-treatment and/or post-treatment composition comprising at least one aminosilicone ranges from 2 to 10.

30. The process according to claim 29, wherein the pH of the pre-treatment and/or post-treatment composition comprising at least one aminosilicone ranges from 3 to 9.

31. The process according to claim 1, wherein the concentration of the at least one aminosilicone in the pre-treatment and/or post-treatment composition ranges from 0.05 to 10% by weight relative to the total weight of the composition.

32. The process according to claim 31, wherein the concentration of the at least one aminosilicone in the pre-treatment and/or post-treatment composition ranges from 0.1 to 7% by weight relative to the total weight of the composition.

33. The process according to claim 1, wherein the pre-treatment and/or post-treatment composition is left to act on the keratin fibers for a period of time ranging from 1 to 60 minutes.

34. The process according to claim 33, wherein the pre-treatment and/or post-treatment composition is left to act on the keratin fibers for a period of time ranging from 3 to 30 minutes.

35. The process according to claim 1, wherein the pre-treatment and/or post-treatment composition further comprises at least one additive chosen from vitamins and derivatives thereof, provitamins, antioxidants, essential oils, wetting agents, silicone and non-silicone sunscreens, preserving agents, sequestering agents, pearlescent agents, pigments, moisturizers, antidandruff agents, anti-seborrhoeic agents, plasticizers, hydroxy acids, electrolytes, solvents and fragrances.

36. The process according to claim 35, wherein the vitamins and derivatives thereof are chosen from vitamin E, vitamin E acetate, vitamin C and its esters, B vitamins, vitamin A alcohol and retinol, and vitamin A acid and retinoic acid and derivatives thereof.

37. The process according to claim 35, wherein the provitamins are chosen from panthenol, vitamin A palmitate, niacinamide, and ergocalciferol.

38. The process according to claim 1, wherein the keratin fibers are hair.

39. A pre-treatment and/or post-treatment cosmetic composition for pre-treatment and/or post-treatment in the permanent reshaping of keratin fibers comprising, in a cosmetically acceptable medium in said composition, at least one aminosilicone in non-microemulsified form chosen from aminosilicones of formulas (I) and (II) below:

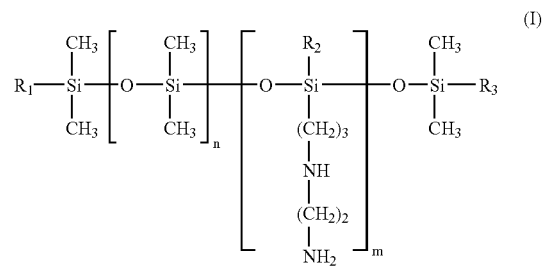

wherein in formula (I):
  m and n are numbers such that the sum (n+m) ranges from 1 to 1 000,
  n is a number ranging from 0 to 999 and m is a number ranging from 1 to 1 000;
  $R_1$, $R_2$, $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

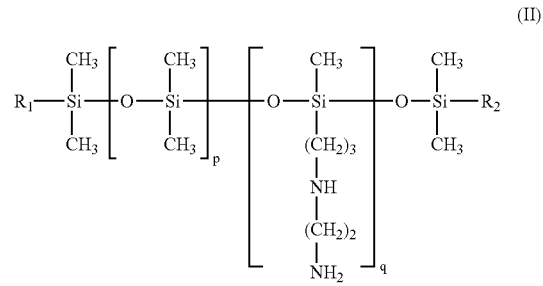

wherein in formula (II):
  p and q are numbers such that the sum (p+q) ranges from 1 to 1 000,
  p is a number ranging from 0 to 999 and q is a number ranging from 1 to 1 000;
  $R_1$, $R_2$, which may be identical or different, are chosen from hydroxyl and $C_1$-$C_4$ alkoxy radicals, wherein at least one of the radicals $R_1$ and $R_2$ is chosen from $C_1$-$C_4$ alkoxy radicals.

* * * * *

UNITED STATES PATENT AND TRADEMARK OFFICE
CERTIFICATE OF CORRECTION

| | | |
|---|---|---|
| PATENT NO. | : 7,510,705 B2 | Page 1 of 1 |
| APPLICATION NO. | : 11/524512 | |
| DATED | : March 31, 2009 | |
| INVENTOR(S) | : Devin-Baudoin et al. | |

It is certified that error appears in the above-identified patent and that said Letters Patent is hereby corrected as shown below:

In the claims:

Claim 28, column 9, line 40, "according claim" should read --according to claim--.

Signed and Sealed this

Nineteenth Day of May, 2009

JOHN DOLL
*Acting Director of the United States Patent and Trademark Office*